United States Patent [19]

Athayde et al.

[11] Patent Number: 5,169,390
[45] Date of Patent: Dec. 8, 1992

[54] OSMOTIC INFUSION DEVICE

[76] Inventors: Amulya L. Athayde, 338 Oak St., Apt. 12, Mountain View, Calif. 94041; Rolf A. Faste, 90 Peter Coutts Cir., Stanford, Calif. 94305

[21] Appl. No.: 526,129

[22] Filed: May 21, 1990

[51] Int. Cl.$^5$ ............................................. A61M 5/14
[52] U.S. Cl. .................................... 604/141; 604/151; 604/892.1; 128/DIG. 12
[58] Field of Search ....................... 604/890–892, 604/896, 51–53, 130–133, 150–153, 93, 96, 140, 141

[56] References Cited

U.S. PATENT DOCUMENTS

| 3,760,805 | 9/1973 | Higuchi . | |
|---|---|---|---|
| 4,034,756 | 7/1977 | Higuchi et al. . | |
| 4,191,181 | 3/1980 | Franetzki et al. . | |
| 4,193,398 | 3/1980 | Refson . | |
| 4,201,207 | 5/1980 | Buckles et al. . | |
| 4,340,048 | 7/1982 | Eckenhoff | 604/890.1 |
| 4,398,908 | 8/1983 | Siposs . | |
| 4,474,575 | 10/1984 | Eckenhoff et al. | 604/131 |
| 4,525,164 | 6/1985 | Loeb et al. . | |
| 4,552,561 | 11/1985 | Eckenhoff et al. | 604/896 |
| 4,596,575 | 6/1986 | Rosenberg et al. . | |
| 4,838,862 | 6/1989 | Faste | 604/141 |
| 4,898,582 | 2/1990 | Baker et al. | 604/892.1 |

OTHER PUBLICATIONS

M. J. Sefton et al, "Controlled Release Micropump for Insulin Administration", Ann. Biomed. Eng., vol. 7, pp. 329–343, (1979).
J. Bottino et al., "Continous Intravenous Arabinosyl Infusions Delivered by a New Portable Infusion System", Cancer, vol. 43, pp. 2197–2201, (1970).
S. Rose et al., "A Continuous Long-Term Injector", Austral. J. Biol., vol. 33, pp. 415–420, (1955).
Product Brochure, Pump Model AS*2F, Auto-Syringe, Inc. Hookset, N.H.
Product Brochure, Pump Model AS*3B, Auto-Syringe, Inc. Hookset, N.H.
Product Brochure, Pump Model AS*5B Auto-Syringe, Inc. Hookset, N.H.
Product Brochure, Pump Model ML6, Cormed, Inc., Middleport, N.Y.

Primary Examiner—C. Fred Rosenbaum
Assistant Examiner—Chalin Smith
Attorney, Agent, or Firm—Anthony J. Castro

[57] ABSTRACT

A portable infusion device assembly where the drug is contained in a separate or separatable pouch in pressure transmitting relationship with a driving medium. The driving medium is pressurized by activation of osmotic pump, and the rate of delivery of the drug is regulated by a rate controlling means. Manufacture and sterilization of the infusate containing pouch separately from the other components of the systems to facilitates construction of sterile infusion pumps and provides an additional measure of safety.

21 Claims, 7 Drawing Sheets

OSMOTIC INFUSION DEVICE

FIELD OF THE INVENTION

This invention relates to controlled release infusion devices, and particularly to small, body-mounted, devices capable of delivering liquids such as drugs, drug solutions or other pharmaceutical agents for prolonged periods, where the liquid is contained in a flexible pouch within the device.

BACKGROUND OF THE INVENTION

Many kinds of parenteral drug therapy require continuous delivery in preference to single or multiple injections. Benefits that accrue from continuous therapy may include, for instance, reduction of toxic or other side effects associated with sharp pulses of drug, significant improvement in the effectiveness of the therapy, and increased patient comfort. The traditional manner of administering sustained parenteral treatments is via intravenous drip. Intravenous drip may be perfectly acceptable in a hospital environment, but it obviously imposes severe restrictions on the activity of the recipient. As a result, considerable research over the last few years has been devoted to the development of small portable infusion pumps. A range of infusion pump devices have appeared, including those with electric or clockwork motors that drive syringe or peristaltic pumps, and others powered by the elastic tension of an inflated balloon, or the vapor pressure of a volatile propellant. Literature incorporated herein by reference describing such pumps includes *Controlled Release Micropump for Insulin Administration*, (M. V. Sefton et al., Ann. Biomed. Eng., Vol. 7, pp. 329–343, 1979), *Continuous Intravenous Arabinosyl Cytosine Infusions Delivered by a New Portable Infusion System*, (J. Bottino et al., Cancer, Vol. 43, pp. 2197–2201, 1979), or product brochures from Auto-Syringe, Inc., Hooksett, N.H. and Cormed, Inc., Medina, N.Y. These infusion pump devices are typically strapped to the wearer, or carried on a belt or in a harness. Also, most infusion pump devices are designed to deliver relatively large quantities of fluid and do not dispense small volumes, of the order of a few milliliters or less, effectively.

An alternative approach that has been exploited to a limited extent is to drive the infuser osmotically, using a Rose-Nelson pump activated by imbibition of water or other driving fluid. The principle of the osmotic pump was originally conceived by Rose and Nelson in the 1950's. (S. Rose and J. F. Nelson, "A Continuous Long-Term Injector," *Austral. J. Exp. Biol.* 33, pp. 415–420 (1955)). A Rose-Nelson pump, typically, consists of three chambers: a salt chamber containing solid salt, a drug chamber, and a water chamber. The salt and water compartments are separated by a rigid membrane permeable to water but impermeable to salt; the salt and drug chambers are separated by a rubber diaphragm. In operation, water is imbibed osmotically into the salt chamber, causing the rubber diaphragm to expand into the drug chamber and forcing the drug out through the delivery orifice. Depending on the salt used, the osmotic pressure developed by this type of pump is usually between 50 and 200 atmospheres. The pressure required to pump the drug from the device is small in comparison, and hence the drug delivery rate remains constant as long as some excess undissolved salt remains in the salt chamber. In comparison with mechanically driven devices, Rose-Nelson pumps are small, reliable, and simple and cheap to manufacture. U.S. Pat. No. 3,604,417 discloses a modification of the Rose-Nelson pump in which a movable piston replaces the elastic diaphragm separating the drug and salt chamber, and both the drug and salt are loaded into the pump as solutions. U.S. Pat. No. 4,474,048 discloses another modification employing an impermeable elastic wall, and a movable end wall that can be screwed in to deliver a pulse dose of the contained drug at any time during the operation of the pump. U.S. Pat. No. 4,474,575 is a variant of 4,474,048 in which the flow rate of the dispensed agent can be varied by altering the area of semipermeable membrane exposed to the water chamber. U.S. Pat. No. 4,552,651 discloses a pump assembly for use with a small osmotic pump that can be filled in advance of use with the active agent to be dispensed. The action of the pump is initiated by filling the lower chamber of the housing with a hydrogel. Once the pump is in action, an optional mechanism for delivering pulse doses can be employed. All these osmotic pumps are self-driven and begin to operate as soon as they are primed with the contents of the several chambers.

U.S. Pat. No. 4,838,862, commonly owned with the present application and incorporated herein by reference in its entirety, describes a portable osmotic infusion pump that can be filled with the agent (typically a drug solution) to be dispensed, the osmotic salt and the driving fluid, and then stored as required. U.S. Pat. No. 4,898,582, also commonly owned with the present application and incorporated herein by reference in its entirety, describes a portable osmotic pump that includes a housing with two side-by-side compartments, where one compartment contains the osmotic pump, and the second compartment contains the driving liquid for the pump. The latter two patents describe osmotic pumps that can be filled with all required fluids, including the drugs to be delivered, stored until needed, and then activated very rapidly on demand. They are therefore excellent systems for use as disposable drug infusion devices.

Many limitations of these infusion pump devices, however, have not yet been addressed or resolved. One limitation of some of these infusion pump systems is that the patient does not have control over activation of the device, or has only limited control. For example, if a device is activated by ingestion, it will begin to release drug as soon as comes into contact with internal fluids. Another limitation is that, for many of these systems, the delivery rate of the infusate is not controlled.

Yet another limitation of some of these infusion pump devices are the problems accompanying long-term storage of the devices. Many substances such as drugs fare poorly when stored, particularly in solution, for a period of time in a delivery device, and particularly for periods of up to two years. The drug may change or deteriorate chemically and pharmacologically, and may precipitate out of solution. [The drug may also be degraded by interaction with other components of the system that diffuse into the drug chamber.] Other problems can occur if the drug solution comes into contact with other components of the device, such as elastic diaphragms, the materials lining the drug chamber, or infusion tubing and needle assemblies. Such designs create a number of storage, material stability, and material biocompatibility problems that are difficult to solve for many of the drug solutions that could conceivably be delivered. Yet another limitation of these devices is the difficulty associated with maintenance of device sterility during production and storage. These aspects are not adequately addressed in available disposable infusion devices and are problems that therefore limit their use.

One means for resolving the problems of maintaining device stability and sterility during long-term infusate storage, described in detail in the present disclosure, is to contain the infusate in a flexible pouch within the device. In one embodiment of the invention, the pouch could be a part of the device that is filled with the infusate during manufacturing, or later, for example by a pharmacist or other person, a short time before the device is used. There are several instances in the patent literature of infusion pumps where the liquid infusate is contained in a separate pouch within the device, for example, U.S. Pat. Nos. 4,191,181, 4,201,207, 4,398,908, and 4,525,164. After activation, these devices develop a pressure that is exerted on the pouch. These devices also typically incorporate a means of controlling the delivery rate of the infusate from the pouch. In many of these devices, however, this delivery rate is controlled by directly regulating the flow of the infusate out of the device, for example, by a flow-rate controlling valve. This configuration presents a number of problems. For example, both the initial sterilization and the maintenance of device sterility are difficult, due to the presence of small compartments and crevices in contact with the infusate that may be difficult for the sterilizing agent to reach. Another problem with direct flow regulation of the infusate fluid is that shear effects created, for example by fluid passing through a valve, may damage molecules in solution in the infusate, for example, proteins or other large molecules. A third problem is that these rate-controlling elements, valves, and the like are relatively unreliable.

One solution to the flow-control problem is to control the infusate delivery indirectly, for example, by controlling the pressure applied to the infusate pouch instead of infusate flow itself. U.S. Pat. No. 4,596,575 discloses a small implantable liquid infusion pump driven by a mechanical pump wherein device activation and flow rate are controlled by electronic regulation of the pump. This device is particularly intended for the delivery of insulin and contains two collapsible reservoirs in a rigid housing, one of which contains the infusate. The space between the outer wall of this reservoir and its rigid housing is filled with the drive liquid. The second reservoir is filled with the drive liquid, and the space between the outer wall of this reservoir and its rigid housing is maintained at subambient pressure. The drive liquid is pumped from the second reservoir into the outer space of the first housing to exert pressure on the first reservoir and thus deliver the liquid infusate. The electronic control unit controls two valves that restrict the flow rate of the drive liquid; thus the infusate does not come in contact with the valving system. This is a complex system, however, containing both mechanical and electrical parts, and is therefore prone to failure. The device is also provided with a separate refill system that may be used to refill the infusate reservoir. This type of refill mechanism presents sterility problems during longterm use, particularly because it is used in an implantable device that cannot be cleaned during use.

U.S. Pat. No. 4,034,756 discloses a small osmotic pump for use in an aqueous environment, such as the gastrointestinal tract, in which the liquid infusate (e.g. a drug) is contained in a flexible bag within the device, and the osmotic fluid exerts pressure directly on the flexible bag to effect liquid delivery. The flexible bag can be filled with the infusate during pump manufacture, or the bag can be filled with the infusate at a later time. This osmotic pump is simple, reliable, and sterilizable. Unfortunately, it can be activated only by exposure to an aqueous environment, and is therefore limited generally to internal use for drug delivery. The device is activated by ingestion or otherwise exposing the device to internal fluids, and rate control is solely a function of the permeability characteristics of the outer canister.

U.S. Pat. No. 4,193,398 describes a similar osmotic infusion pump that is portable and intended for extracorporeal use, i.e. the device is mounted externally. In the principle embodiment of this patent, the infusate is contained in a flexible polymeric bag made of polyvinyl chloride or some like material. An aqueous solution is contained in a second bag, while the osmotic solution is contained in a rigid chamber that encloses the infusate bag. In use, water diffuses through a semipermeable membrane separating the water bag from the osmotic solution chamber, and this water flow produces a pressure on the flexible infusate bag. In the normal mode of use, this device is loaded with the three fluids (the infusate, the osmotic solution, and water) immediately before activation, and then connected to the patient's infusion system. One problem with this embodiment of the device, however, is the sterility problems attendant with filling the device with fluids prior to use. Therefore, this embodiment is primarily suitable for a hospital setting. In another embodiment, a rupturable or removable water-impermeable barrier separates the semipermeable membrane from the osmotic solution. In principle, incorporation of such a barrier into the device would allow it to be loaded with the three fluids, stored for a prolonged period, and then activated when required. In fact, this embodiment would not be practical for several reasons. First, in this embodiment, the osmotic solution and infusate are separated by only a flexible polymeric bag for a period that could be as much as two years or more. (A typical pharmaceutical product has a shelf storage time of at least two years.) Since this is a medical device, complete integrity of the system is an absolute requirement, and contamination of the infusate is unacceptable. It is almost impossible to meet this requirement in the device described in 4,193,398, for diffusion of solutions across the barrier created by the bag material will occur on storage. Second, in this device, the membrane is exposed to water for the entire storage period of the device. Again, this is not tolerable. Semipermeable membrane materials, by their nature, must be made of hydrophilic polymers that are susceptible to slow degradation and hydrolysis by water. This is a well-known problem with the most widely used class of cellulose acetate semipermeable membranes. Thus the membrane, by being exposed to water for the full storage period, would degrade and lose its integrity. Therefore, incorporation of rupturable or removal barrier as an activation means is not useful where the device is meant to be stored for a prolonged period of months or years prior to use.

Each of these references describes a portable infusion pump that incorporates an infusate pouch or reservoir in a specific configuration, and usually with a specific motive force, yet all have problems that have inhibited their use. These include a high cost of manufacture, difficulties with sterilizing the infusate chamber and contents, difficulties in maintaining sterility of the device, and problems with stability of the devices after prolonged storage. As a result, there remains a need for a reliable disposable infusion pump that can be loaded with sterile liquid infusate, that can maintain sterility during prolonged storage, and that can then deliver the infusate following the required pattern of delivery of very low flow rates on demand.

The present invention describes a disposable osmotic infusion pump that is small, light, and convenient for patient use. The novel feature of the pump described in the present disclosure is the method used to package the infusate. In U.S. Pat. Nos. 4,838,862 and 4,898,582, the infusate is separated from the osmotic chamber by an elastic diaphragm that can expand into the chamber containing the infusate and force the infusate from the device. We have discovered that it is possible to incorporate the infusate in a sealed, flexible but not necessarily elastic, pouch that is placed inside the osmotic chamber. This device has a number of advantages, one of the most important being that the infusate pouch can be manufactured, loaded with infusate, sealed, and sterilized in a completely separate operation to the construction of the rest of the pump. This is a considerable production advantage. In addition, with this design, the pouch can be made of nonelastic materials, allowing construction from simple, biocompatible materials that are relatively impervious to invasion by environmental agents such as oxygen, or other components of the device.

SUMMARY OF THE INVENTION

Objects of the Invention

It is an object of the invention to provide a portable controlled release infusion device that can be stored, with or without the infusate, for prolonged periods without deterioration.

It is another object of the invention to provide a portable controlled release infusion device wherein each individual device could potentially be used to deliver any of a variety of different liquids, including different drugs.

It is another object of the invention to provide a portable controlled release infusion device that is inexpensive and straightforward to manufacture.

It is another object of the invention to provide a disposable portable controlled release infusion device.

It is another object of the invention to provide a portable controlled release infusion device that can be activated quickly and simply on demand.

It is another object of the invention to provide a portable controlled release infusion device in which the infusate is easily sterilized and is maintained in sterile and contaminant-free state after prolonged storage.

It is another object of the invention to provide a portable controlled release infusion device that can be stored in a sterile condition for a period of up to two years or longer without impairment of its infusate delivery function.

It is yet another object of the invention to provide for the controlled flow-rate delivery of the liquid infusate from a portable controlled release infusion device.

Other objects and advantages of the invention will be apparent to those of ordinary skill in the art from the description that follows.

DESCRIPTION OF THE INVENTION

Figure 1:
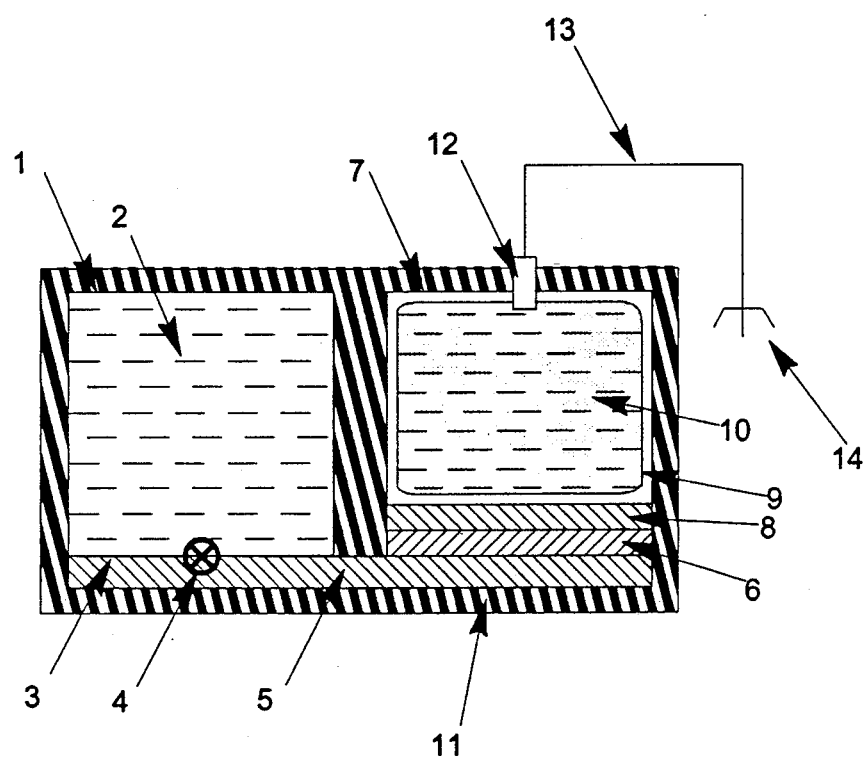
FIG. 1 is a diagram of the basic features of the invention.

To achieve the foregoing objects, the present invention provides a portable osmotic controlled release infusion pump assembly, based on the Rose-Nelson principle. The assembly includes two chambers, where a pouch, an osmotic salt or fluid, and a rate-controlling means are contained in the first chamber, known as the delivery chamber; a driving fluid and activation means for the pump are contained in the second chamber, known as the power chamber and a passage connects the two chambers. The delivery chamber is contained in a housing that restricts movement of the pouch. Preferably, the entire device is contained in a unitary housing so as to protect the device from the environment. The housing can be made of metal or plastic, and would normally be made by any conventional mass-production technique. Housing dimensions will vary according to the volume of the chambers contained. The delivery chamber of the pump houses an infusate pouch that is preferably sterilizable and under neutral pressure. This infusate pouch contains the infusate, preferably in liquid form, and has a minimal free volume in the chamber. The delivery chamber also houses the osmotic salt or osmotic fluid, which is found adjacent to the infusate pouch and in contact with most of the outer surface of the pouch. In a preferred embodiment, the delivery chamber contains a solid osmotic salt, thereby avoiding exposure of the infusate pouch to the osmotic fluid during storage of the device. The delivery chamber also contains the rate-controlling means, which in its preferred embodiment is a semipermeable membrane. The assembly includes a power chamber that contains the driving fluid and a means for activating the device. In a preferred embodiment, the driving fluid is water, and the activating means ruptures a seal separating the driving fluid from the delivery chamber. This position of the seal is preferred because the semipermeable membrane is thus stored dry and is not exposed to the driving fluid, which might degrade the membrane on long term storage. Activation of the device causes the delivery of the driving fluid to the delivery chamber, where it will pass through the rate-controlling means and cause formation or augmentation of the osmotic fluid. This osmotic fluid will then exert pressure on the infusate delivery pouch. The resulting delivery rate of the infusate to the needle assembly is thus dependant on the pressure created in the delivery chamber. A number of different activating means are disclosed in co-owned U.S. Pat. Nos. 4,838,862 and 4,898,582, herein incorporated by reference, including valves and the like, are encompassed in the scope of this invention.

The invention described is normally intended to deliver low flow rates, e.g. 0.5 to 10-20 ml per day, of infusate solution to the patient, and thus is primarily intended for subcutaneous, as opposed to intravenous, delivery. Higher or lower delivery rates could be achieved, however, by varying the osmotic salt or the material, surface area, or thickness of the semipermeable membrane. The infusion apparatus as herein described may be used for intravenous therapy where the flow rates of infusate are compatible with the intended intravenous therapy.

A characteristic of this invention is that the delivery chamber contains a pouch that contains the infusate. Containment of the infusate in an infusate pouch in the delivery chamber is advantageous because it makes it possible for the rest of the pump assembly to be fabricated and assembled separately from this pouch, thus simplifying manufacture of the infusion device. In one embodiment, the infusate pouch and its contents are stored separately from the rest of the pump assembly, thus greatly increasing the shelf life of the pump assembly. The infusate pouch and infusate are preferably sterilized before insertion into the pump assembly in such a manner that the infusate is not changed, e.g., the drug is not changed chemically or pharmacologically. One means for such sterilization is radiation. Alternate means for such sterilization include heat sterilization, or ethylene oxide sterilization, or the infusate may be filled into the infusate pouch using aseptic technique to maintain sterility. Since the infusate pouch and the pump are prepared separately, they can be sterilized separately using whatever method of sterilization is best suited to each component.

The infusate pouch is made of a flexible material that will have an extended shelf life and will be impermeable to both the infusate contained (on its inner surface) and the driving fluid (on its outer surface). The material used for manufacture of this pouch should thus be flexible enough that pressure can be applied to cause delivery of the infusate. Elastic materials are not preferred because most elastic materials would be vulnerable to diffusion of the infusate out of the pouch, or of diffusion of the driving fluid into the pouch. In addition, elastic materials would typically be more vulnerable to attack and degradation caused by the infusate solution. Therefore, preferred materials for the infusate pouch are polyethylenes, polypropylenes, Teflon ® (E. I. Du Pont de Nemours & Co., Wilmington, DE), Barex ® (BP Chemicals International, Cleveland, OH), Tedlar ® (Du Pont), and polyfoil laminates of materials such as polyethylene (facing the drug solution) and aluminum foil outside the pouch. In a preferred embodiment of the invention, the pouch is contained in the delivery chamber containing solid osmotic salt, and liquid enters the delivery chamber only after the device is activated. This preferred embodiment simplifies storage of the device, because osmotic fluid contacts the outside of the pouch only during the infusate delivery period, typically from one to ten days. The pouch material must prevent the diffusion of the osmotic fluid into the infusate pouch for the maximum time of the delivery period. If an osmotic fluid is kept in the delivery chamber during device storage, the requirements for impermeability of the pouch increase by approximately 100-fold.

The infusate contained in the pouch may be in its final fluid form, ready for delivery. In some instances, however, it may be preferable to store the infusate, e.g. a drug, in a lyophilized or otherwise desiccated form, in order to prolong the storage time of the device. This would be of particular interest if the infusate pouch were to be stored as part of the pump assembly for the entire shelf life of the device. Therefore, in an alternate embodiment, the infusate pouch will be segmented into two compartments. One compartment contains a lyophilized form of the infusate, and the other compartment contains a pharmaceutically acceptable liquid solvent. In this preferred embodiment, a seal between the two compartments would be broken by the user, or by a pharmacist, before or during activation of the pump for use. To protect the infusate from degradation by diffusion of any foreign substances into the pouch during storage, and in particular the solvent, the seal must be made of impermeable materials. Preferred materials include metallized foil, metallized plastic film, and the like. This embodiment allows for storage of the infusate for long periods of time while insuring that the sterility of the pouch environment is not violated. In an alternate embodiment, the infusate pouch will contain a lyophilized form of the infusate, and the user or pharmacist will add a liquid solvent to the pouch either before or during activation of the pump for use.

In addition to containing the infusate pouch, the delivery chamber also contains the osmotic salt or fluid, and the rate-controlling means. In a particularly preferred embodiment, the delivery chamber contains a solid osmotic salt, thereby avoiding exposure of the infusate pouch to the osmotic fluid during storage of the device. Preferred osmotic media are solid tablets or powders of salts, such as sodium chloride, magnesium sulfate, and sodium sulfate, salt solutions, such as sodium chloride solution; and water soluble organic liquids such as polyethylene glycol can also be used. Some sugars can also be used: dextrose, lactose, and fructose, for example, are all good candidates. The permeability of water across the semipermeable membrane is proportional to the osmotic pressure difference across the membrane, as described in Baker, R. W., *Controlled Release of Biologically Active Agents*; John Wiley & Sons: New York, 1987, p. 156. Typical salts that might be used, and their osmotic pressures, are listed in Table 1.

Activation of the device initiates the delivery of the driving fluid from the power source to the delivery chamber, where it passes through the rate-controlling means and surrounds the infusate pouch. Osmotic pressure is created when the driving fluid enters the delivery chamber, exerts pressure on the infusate pouch, and forces infusate out of the pouch and into the delivery tube and needle assembly.

In order for the device to function effectively, the delivery chamber must be absolutely fluid tight, so that the osmotic pressure generated forces infusate out of the pouch and thus reduces its volume. In addition, the infusate pouch should fit as snugly as possible in the delivery chamber, with as little free space as possible. This snug fit is somewhat difficult to obtain for the embodiment in which the osmotic salt is stored in tablet form in the delivery chamber. Any free space in the delivery chamber will be occupied by air. If some air is trapped in the delivery chamber, however, it presence will delay the commencement of infusate delivery after activation of the device. As the osmotic fluid is created, it will exert pressure on the air and compress it, thus creating a lag between the time of device activation and the time of initial infusate delivery. In contrast, an osmotic solution will assume the shape of its container and will adhere, at least to some extent, to the infusate pouch as it is inserted in the chamber.

TABLE 1

| Salt | Vapor Pressure of Saturated Solution @ 20° C. in (% humidity) | Osmotic Pressure @ 20° C. in atm | Solubility in g 100 g H₂O |
|---|---|---|---|
| NaCl | — | ~378.2 @ 25° C. | 36.5 |
| Pb(NO₃)₂ | 98 | 27 | 58.9 |
| KCl | — | ~216.7 @ 25° C. | 34 |
| Na₂HPO₄.12H₂O | 95 | 68.4 | 4.4 |
| NH₄H₂PO₄ | 93 | 96.8 | 128.4 |
| ZnSO₄.7H₂O | 90 | 140.6 | 57.7 |
| K₂CrO₄ | 88 | 170.6 | 64.6 |
| KHSO₄ | 86 | 207.2 | 57.4 |
| KBr | 84 | 232.6 | 68.3 |
| (NH₄)₂SO₄ | 81 | 281.1 | 74.1 |
| NH₄Cl | 79 | 314.5 | 35.7 |
| Na₂C₂H₃O₂.3H₂O | 76 | 366.1 | 50.6 |
| NaClO₃ | 75 | 383.8 | 106.8 |
| NaNO₂ | 66 | 554.4 | 84.4 |
| NaBr.2H₂O | 58 | 726.8 | 94.5 |
| Mg(NO₃)₂.6H₂O | 56 | 773.6 | 72.8 |
| NaCr₂O₇.2H₂O | 52 | 872.4 | 176.8 |
| Zn(NO₃)₂.6H₂O | 42 | 1157.4 | 118.3 |
| CaCl₂.6H₂O | 31 | 1562.6 | 85.6 |
| KC₂H₃O₂ | 20 | 2147.3 | 219.2 |
| LiCl.H₂O | 15 | 2531.1 | 84.8 |

The rate-controlling means controls the flow of driving fluid into the delivery chamber. One advantage of the present invention is that the rate-controlling means is inherent in the pump design, because with traditional valving it is difficult to reliably control the low flow rates (up to 10-20 ml per day) required for infusion therapy. It is another advantage of the present invention that the fluid that is directly controlled is not the infusate, due to attendant problems with maintaining sterility of the rate-controlling means, and the need to avoid shear effects on the infusate.

In a preferred embodiment, the rate-controlling means is a semipermeable membrane that is permeable to the driving fluid and impermeable to the osmotic salt or solute. When the pump is in use, the rate of pumping of fluid to the delivery chamber is thus controlled by the permeation properties of this membrane. Cellulose acetate is an especially preferred membrane material for this application because its water permeability is high and can be modified easily by varying the degree of acetylation of the polymer. As discussed in U.S. Pat. No. 4,077,407 and U.S. Pat. No. 4,838,862, each incorporated herein by reference in its entirety, the permeability of cellulose acetate membranes can be increased further by adding plasticizers to the polymer to increase the water diffusion coefficient, or by adding hydrophilic flux enhancers, which increase the water sorption of the membrane. Some hydrophilic plasticizers serve both purposes. The effect of the hydrophilic plasticizer, polyethylene glycol, on the osmotic water permeability of cellulose acetate membranes is substantial; water permeability is increased more than fourfold by the addition of polyethylene glycol. Addition of the hydrophilic polymer, hydroxybutyl methyl cellulose, to the cellulose acetate membrane has a similar effect. Thus certain membrane materials can be tailored so that their permeability characteristics are made suitable for the particular application at hand, i.e. so that, in the device created, the infusate is delivered to the patient at the desired flow rate.

A preferred choice for the driving fluid is water or another osmotically weak solution. Upon activation of the device by breaking a seal or other means, the driving fluid is released from the power chamber, travels through the passage connecting the two chambers, and contacts the semipermeable membrane and passes through it into the delivery chamber. In one embodiment, a wick is present in the passage connecting the two chambers, and activation of the device allows the driving fluid to be absorbed by the wick. The wick material may be filter paper, or any porous or spongy material capable of absorbing and transporting the driving fluid.

In one embodiment, the power chamber contains the driving fluid and an activation means. Alternately, the power chamber may also contain the rate-controlling means. The activation means initiates the delivery of the driving fluid to the delivery chamber. Thus, the activation means allows for activation of the pump at the user's discretion. In another embodiment, the activation means ruptures a seal separating the driving fluid from the delivery chamber. This rupturing of the seal thus allows the driving fluid to enter the passage connecting the power chamber to the delivery chamber, to pass through the rate-controlling means, and to enter the delivery chamber.

The infusate leaves the infusate pouch through a port and tube. The end of the tube is adapted for use with a skin-piercing needle or a standard commercial subcutaneous drug delivery set, for example, the Sub-Q-Set ®(-Travenol Laboratories, Deerfield, IL). Alternately the tube may be inserted into one of the normal body orifices, or into a previously established indwelling catheter.

The device assembly can be attached to the body of the wearer by means of a biocompatible adhesive coating on the base of the assembly, or by adhesive strips or overlays, and does not require the use of straps, belts, or other carrying garments. The device may be attached anywhere on the body that is convenient, either immediately adjacent to the delivery site, or at a point distant from that site.

The foregoing general description and the following detailed description are exemplary and explanatory, but are not restrictive of the invention.

Because the device described in the present invention is small and simple, it is particularly suitable for delivering small infusate volumes. The pump assembly of this invention, while it can be tailored for a range of infusate volumes and dosage rates, is particularly useful where the total infusate volume to be dispensed is of the order of 0.5 to 10-20 ml, and the delivery time is one to seven days. Thus the invention enables the administration of highly potent substances, such as peptide drugs of various kinds, heparin, insulin, analgesics, anesthetics, corticosteroids, immunosuppressants, antineoplastics, antibacterials, and antidotes to chemical or biological poisons without subjecting the patient to repeated injections or requiring immobilization the patient with continuous intravenous therapy. A number of drug are particularly suited for delivery via the instant infusion device including but not limited to heparin, insulin, chemotherapeutic agents such as fluorouracil, cisplatin, antibiotics such as adriamycin, oncovin, bleomycin, vancomycin, tobramycin, antinauseants such as haldol, benadryl, antivirals such as gancyclovir, and analgesics such as morphine, codeine, fentanyl, ketorolac, dilaudid and the like.

The infusion assembly can be filled with all the required ingredients and stored for periods of months or years without deterioration. In one embodiment, the infusate is stored in the infusate pouch separately from the rest of the pump assembly. When required, the patient or pharmacist can insert the infusate pouch into the device, and the device can then be activated on demand by the user.

DETAILED DESCRIPTION OF THE INVENTION

Definition of terms.

The term "drug" as used herein denotes any medication (as defined, below); composition in any way affecting any human or animal entity; substance to be assimilated by any human being or animal for its nourishment or for regulating its growth; substance exhibiting any of the above activities to be directly applied to the habitat, surroundings or environment of any of the above organisms; and substances having any other effect on any other environment, especially any aqueous environment.

Therefore, suitable drugs for use with the dispenser of this invention include, without limitation, those that are generally capable of:

1. Preventing, alleviating, treating, or curing abnormal or pathological conditions of the living body by such means as destroying a parasitic organism or limiting the effect of the disease or abnormality by chemically altering the physiology of the host or parasite;

2. Maintaining, increasing, decreasing, limiting or destroying a physiologic body function, e.g. vitamin compositions, sex sterilants, fertility inhibitors, fertility promoters, growth promoters, and the like;

3. Diagnosing a physiological condition or state;

4. Controlling or protecting an environment or living body by attracting, disabling, inhibiting, killing, modifying, repelling, or retarding an animal or microorganism, such as food and nonfood baits, attractants and lures, biocides, pesticides, algicides, parasiticides, rodenticides, insecticides, fungicides, and the like;

5. Preserving, disinfecting, or sterilizing; and

6. Controlling or affecting generically an environment, as by introducing a catalyst or metering a reactant into a reacting chemical system, or by effecting any chemical process therein, such as fermentation, including propagation and/or attenuation of a microorganism.

DETAILED DESCRIPTION OF THE FIGURES

Referring now to the drawings, a general plan of the invention is shown in FIG. 1. The device shown is based on the Rose-Nelson osmotic pump. The power chamber 1 contains the driving fluid 2 and an activation means 4 for contacting the driving fluid 2 with semipermeable membrane 6. Use of the activating means to rupture seal 3 causes delivery of the driving fluid 2 through the separating barrier or seal 3 into a passage 5 between the chambers, and into the delivery chamber, 7. The delivery chamber contains the rate-controlling means 6, osmotic salt 8, and the infusate pouch 9 containing infusate 10. It is a particular advantage of this system that the rate-controlling means is inherent in the design, because it is difficult to control the low flow rates (up to 10–20 ml per day) using conventional valve technology. In a preferred embodiment, the rate-controlling means 6 is a semipermeable membrane that allows passage of water but does not allow passage of osmotic salt or osmotic solute. A wide range of appropriate solutes for use in osmotic pumps is disclosed in U.S. Pat. No. 4,034,756, which is incorporated herein by reference. Preferred salts are sodium chloride, potassium chloride, magnesium sulfate, and sodium sulfate. Alternately, the delivery chamber may contain an osmotic fluid instead of the osmotic salt.

It is a requirement of this invention that delivery chamber 7 be sealed so that fluid entering this chamber does not leak from the pump. Thus, as driving fluid is imbibed osmotically into the delivery chamber, the expanding osmotic fluid will exert pressure on the infusate pouch 9. Therefore, the infusate pouch, which contains the infusate 10, must be made of a flexible material. Elastic materials, however, are normally not used, because most elastic materials are poor diffusion barriers and could allow diffusion of the infusate out of the infusate pouch, or of diffusion of the driving fluid into the infusate pouch. In addition, elastic materials are typically more vulnerable to attack and degradation caused by the infusate solution. Therefore, preferred materials for the infusate pouch 9 are inert polymers such as polyethylene, polypropylene, and copolymers thereof, Teflon ® (E. I. Du Pont de Nemours & Co., Wilmington, DE), Barex ® (BP Chemicals International, Cleveland, OH), Tedlar ® (Du Pont), and polyfoil laminates of materials such as polyethylene (facing the infusate solution) and aluminum foil outside the infusate pouch. Power chamber 1, the passage 5 connecting the power chamber and the delivery chamber, and the delivery chamber 7, as shown in FIG. 1, are contained in a protective housing 11, which is rigid and should be nonirritating to the skin and nonreactive and impervious to the salts, solutions, and agents contained. Preferred materials for housing 11 are stainless steel, aluminum, polyolefins, polycarbonate and the like. The delivery port of the infusate pouch is provided with a dispensing nozzle 12, which serves as an attachment point for the infusate delivery tube 13. A needle assembly 14 is connected to the other end of delivery tube 13, and provides the means of direct attachment to the patient. The needle assembly may be a skin-piercing needle or a standard commercial subcutaneous delivery set, for example, the Sub-Q-Set ® (Travenol Laboratories, Deerfield, IL.). Alternately the infusate delivery tube may be inserted into one of the normal body orifices.

Figure 2:
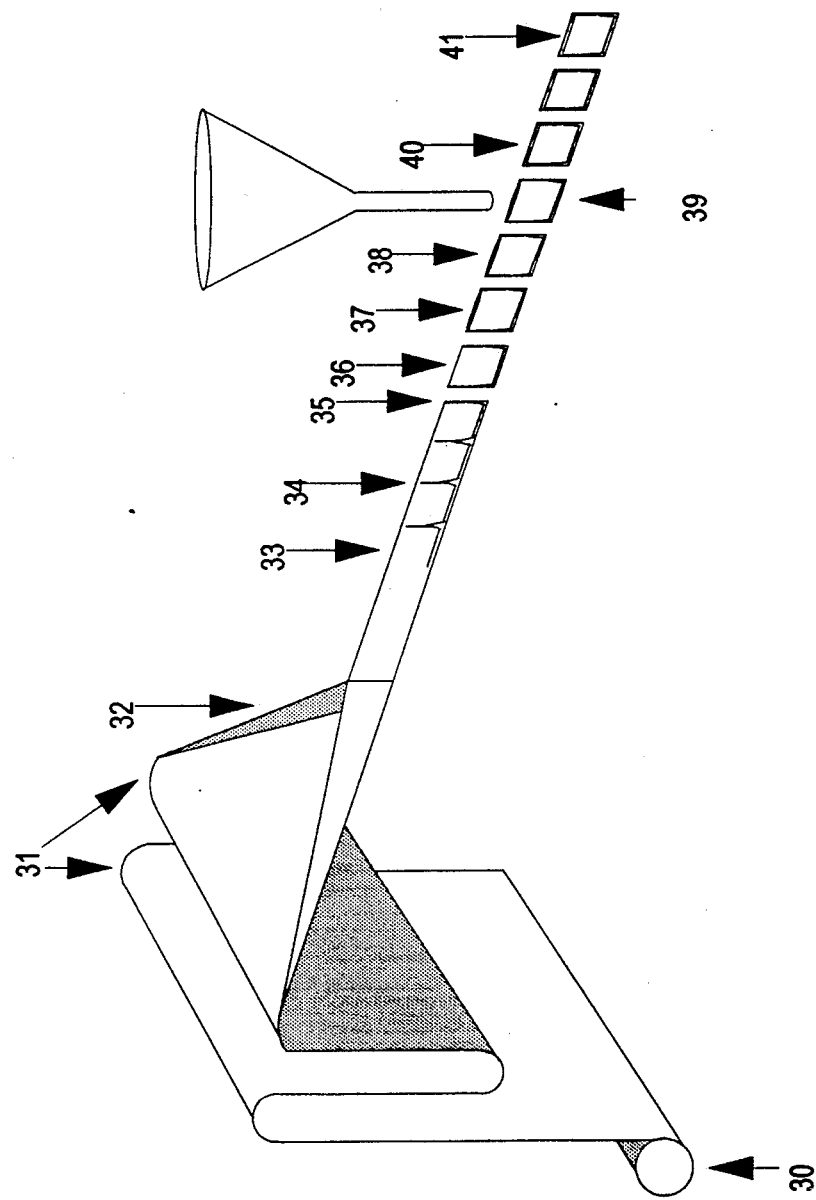
FIG. 2 is a diagram of a packaging process for creating, filling, and sealing the infusate pouch aseptically and separately from the pump assembly.

It is a major advantage of this invention that the infusate solution is in contact with inert, stable, sterilizable, nonleaching materials, which are essentially impervious to contaminants from the outside environment. In one embodiment, the infusate pouch 9 is formed and filled with infusate solution in a single operation using a heat-sealing form-fill-and-seal technology widely used industrially. This form-fill-and-seal technology is used, for example, to form small polyfoil bags containing foods such as ketchup and mustard or transdermal drug delivery systems. This technology is amenable to very high production rates at low cost and be carried out under aseptic conditions. FIG. 2 illustrates an embodiment of this type of packaging system. FIG. 2 is a diagram of a packaging process for creating, filling, and sealing the infusate pouch aseptically and separately from the pump assembly. It presents an overview of the process that illustrates how a roll of packaging material is formed and filled, how seals are created in the material, and how the packages are separated into individual pouches. Web roll 30 holds a rolled supply of the pouch material, ready to be unrolled into tensioning unit 31 and plow assembly 32, which folds the strip of material in half. At station 33 the strip is sealed at the fold to create the bottom fold, and at station 34 the side sealing is accomplished at desired intervals. At station 35 the pouches are cut into individual units, and at stations 36 and 37 the pouches are positioned and opened to receive the infusate. At station 38 the pouches are formed to prepare them for filling, and at station 39 the pouches are filled with infusate. In one embodiment, a simple funnel system is used to deliver the infusate to the individual pouches. In another embodiment, an auger feeder is used for nonfree-flowing powders and granules. At station 40 the pouches receive their top seals, and at station 41 the completed pouches are ready to be removed from the system and delivered to the next packaging station.

Figure 3:
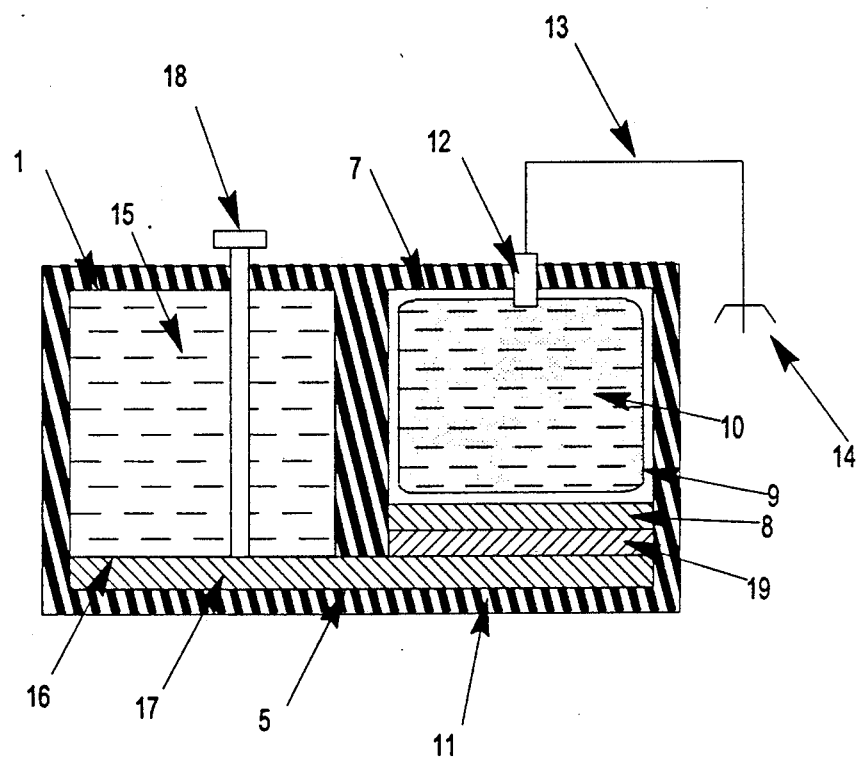
FIG. 3 is a diagram of an embodiment of the invention in which the activating means is a plunger or other mechanism breaking an impermeable foil seal, and the rate-controlling means is a semipermeable membrane.

FIGS. 3, 4, 5, 6 and 7 are illustrations of some further embodiments of the general plan illustrated in FIG. 1. FIG. 3. illustrates a particular embodiment of a Rose-Nelson osmotic pump. The driving fluid for this pump is normally water 15 although any liquid capable of generating an osmotic pressure in conjunction with the osmotic fluid could be used. Before activation of the device, water 15 is contained in the power chamber 1 which is separated by a seal 16 from contact with the wick 17, semipermeable membrane 19, and the osmotic salt 8. In this embodiment, seal 16 is made from metal foil, metallized film or the like. In another embodiment, seal 16 may be provided with release pins that, when broken, allow the power chamber to be moved within the device so that water 15 comes into contact with wick 17. Seal 16 is ruptured immediately prior to use by an activation means that breeches the seal. In the device shown in FIG. 3, seal 16 is attached to plunger 18. Thus when plunger 18 is rotated, the seal is ripped and water 15 contacts and wets wick 17. Wick 17 is contained in the passage 5 between the two chambers and can be made of filter paper or any porous or spongy material capable of absorbing and transporting water or the corresponding driving fluid to the rate controlling membrane. Water wets wick 17, and is transported thereby to contact the semipermeable membrane 19 in delivery chamber 7, which contains osmotic salt tablet 8, infusate pouch 9, and infusate 10. Alternately the delivery chamber may contain an osmotic fluid instead of osmotic salt tablet 8. However, it is preferred that the device contain an osmotic salt tablet, so that during storage the infusate pouch 9 is not in prolonged contact with osmotic fluid. The delivery rate of the pump depends on the area, thickness, and permeability characteristics of semipermeable membrane 19. Hence the choice of a suitable membrane material is essential to good performance of the pump. Membranes made from one of the cellulose esters or ethers, such as cellulose acetate or cellulose butyrate are preferred. Cellulose acetate has long been used in membrane applications and can be formed easily into thin films of reproducible thickness with standard solution casting techniques, making it a particularly preferred choice. Other choices for membrane materials include polyamides; nylon 6; nylon 6—6; aromatic polyamides, for example, the aromatic polyamide sold under the name Nomex ® (Du Pont); cellulose acetate butyrate; ethylcellulose; cellulose nitrate; blends of cellulose acetates of various degrees of acetylation; or various types of cellulosic esters and ethers. Many other semipermeable membranes are known and discussed, for example, in the book *Reverse Osmosis and Synthetic Membranes: Theory-Technology-Engineering*, Sourirajan, S Ed., National Research Council Canada; Division of Chemistry, National Research Council of Canada, Ottawa. Canada, 1977, NRCC No. 15627 and herein incorporated by reference. Osmotic pressure is developed by diffusion of water 15 through semipermeable membrane 19 into the delivery chamber and exerted on infusate pouch 8, and the infusate 10 is delivered as described in FIG. 1 above.

Figure 4A:
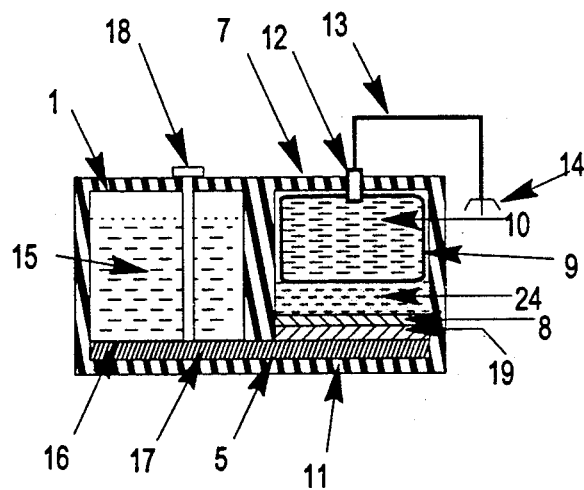
FIG. 4 is a diagram illustrating the operating principle of the invention.
Figure 4B:
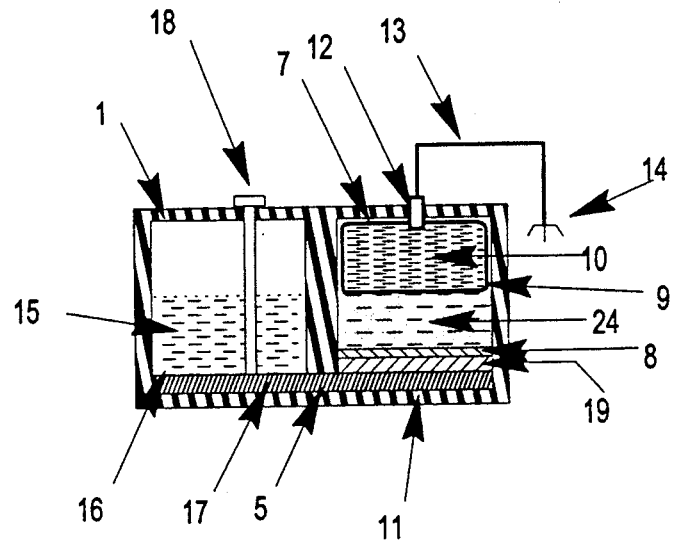
Figure 4C:
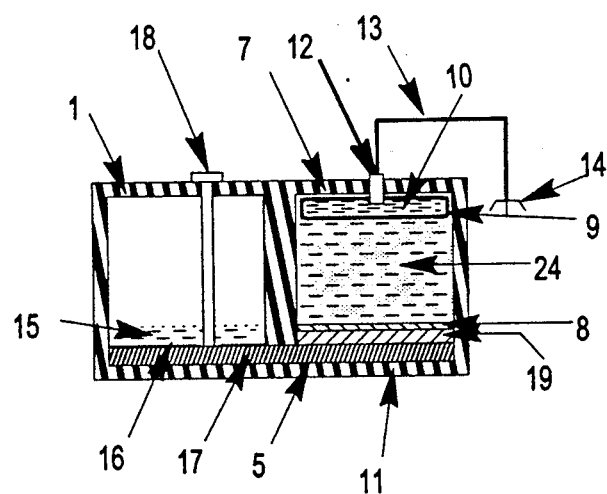

FIG. 4 illustrates the operation of the embodiment of the device described in FIG. 3. In FIG. 4a seal 16 is broken by the activation means, in this case, plunger 18. Driving fluid 15 is absorbed by wick 17 and begins to penetrate semipermeable membrane 19. Entrance of driving fluid into the delivery chamber 7 causes dissolution of osmotic salt 8, and also results in creation of osmotic fluid 24. Thus the osmotic fluid begins to exert pressure on infusate pouch 9. In FIG. 4b, driving fluid 15 continues to pass through the wick 17 and semipermeable membrane 19 and into the delivery chamber, thereby creating more osmotic fluid. Pressure exerted on infusate pouch 9 by the transfer of fluid, causes infusate 10 to be forced out of the pouch, through dispensing nozzle 12, delivery tube 13, and needle assembly 14, and into the patient. In FIG. 4c, this process has continued to the point where most of water 15 has left the power chamber, and the pressure created by osmotic fluid 24 has forced most of infusate 10 out of the pouch. As long as there is remaining driving fluid and undissolved osmotic salt 8, however, pumping activity will continue until either the supply of infusate or driving fluid is exhausted.

Figure 5:
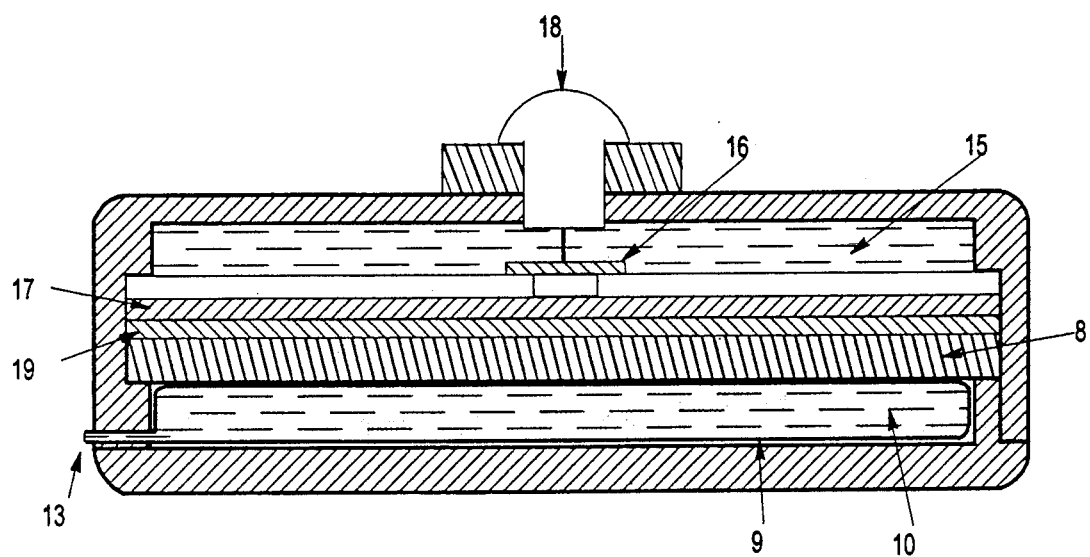
FIG. 5 is a diagram illustrating the operating principle of the invention.

An alternative configuration of the activation mechanism is illustrated in FIG. 5. In this device, seal 16 is broken when plunger 18 is depressed. This action brings water 15 in contact with wick 17.

Figure 6A:
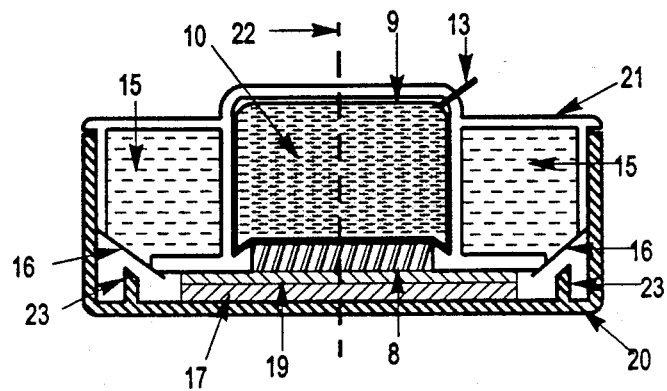
FIG. 6 is a diagram illustrating the operating principle of the invention.
Figure 6B:
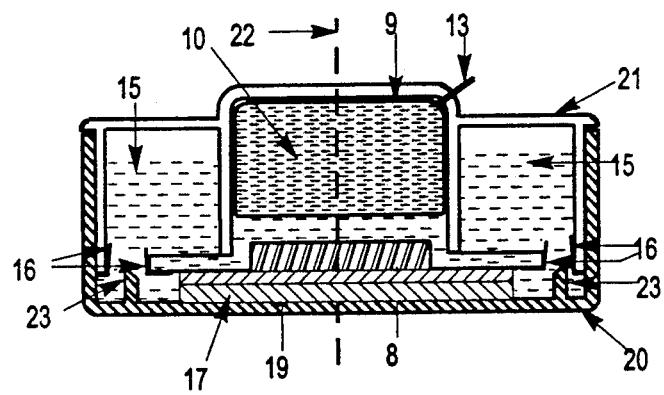

Yet another alternative configuration of the activation mechanism is shown in FIG. 6. This embodiment of the invention is constructed in two sections, 20 and 21, that are rotatable about control axis 22. Before activation, seal 16 is above the level of pins 23 and prevented from contact with pins 23. Activation occurs when the top section lowered so that is rotated so that the seal now comes in contact with the pin. Rotation of the top portion completes the activation step by further rupture and tearing of the seal. The breaking of seal 16 allows water 15 to come in contact with wick 17.

Figure 7:
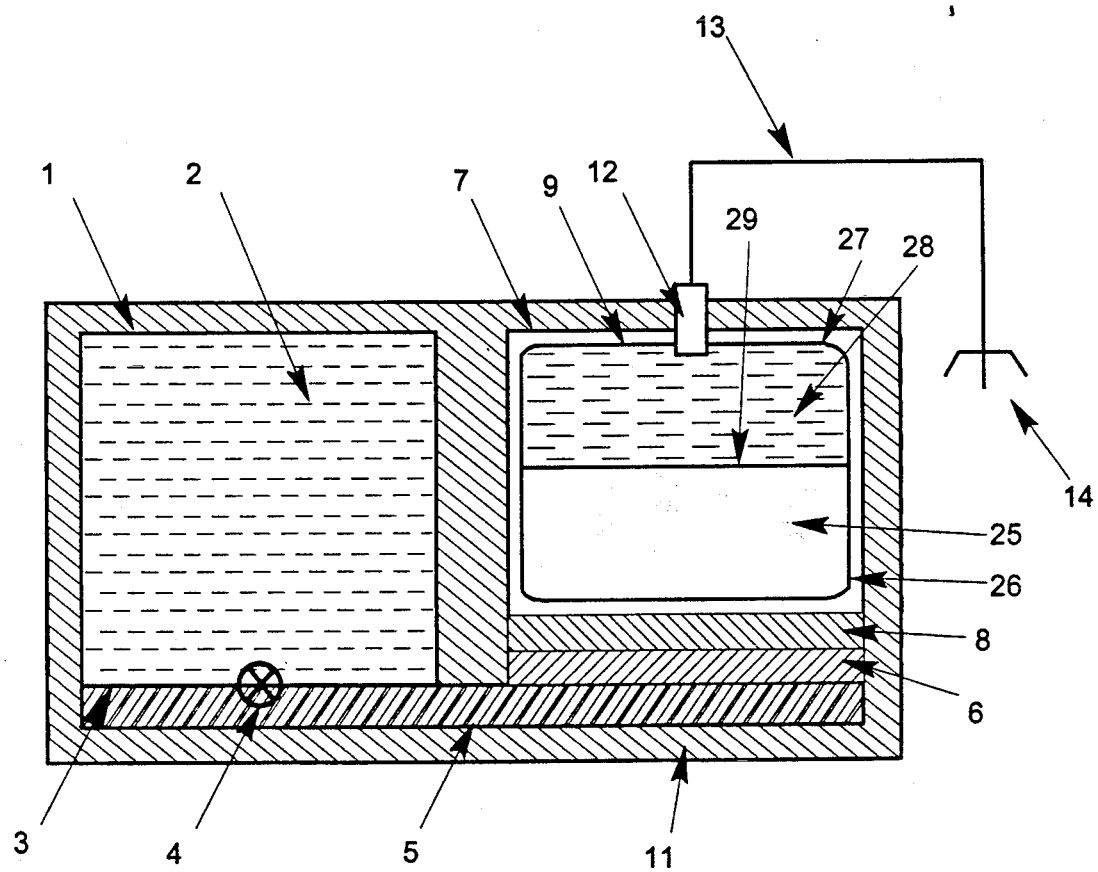
FIG. 7 is a diagram of an embodiment of the invention for which the infusate is contained in lyophilized form in a pouch with two compartments, with a seal separating the infusate from a liquid solvent.

Another embodiment of the invention, which is shown in FIG. 7, is a modification of the design of infusate pouch 9 that appears in FIGS. 1 and 3. In this embodiment, shelf life of the device containing drug is prolonged by storing the infusate 25 in lyophilized or otherwise desiccated form in two compartments of infusate pouch 9. Compartment 26 of infusate pouch 9 contains lyophilized infusate and is separated from compartment 27 of pouch 9, which contains liquid solvent 28 for lyophilized infusate 25, by rupturable seal 29. This seal 29 must be impermeable to both the lyophilized infusate 25 and the liquid solvent 28, therefore, a preferred material for this seal is a metallized foil, metallized plastic film, or the like. Seal 29 is ruptured by the user immediately before or during activation of the device, to allow mixing of lyophilized infusate 25 and liquid solvent 28 before delivery of the infusate to the patient.

We claim:

1. A portable infusion device assembly comprising:
   a. a power chamber comprising:
      a pressure-generating means comprised of:
         a driving fluid;
         an activation means for initiating the action of aforesaid pressure-generating means;
   b. a delivery chamber comprising:
      a pouch containing infusate and a dispensing nozzle, an osmotic salt or fluid,
      a rate-controlling means for regulating the volume change of aforesaid pouch;
   c. a fluid-transport means in liquid transmitting relationship between the aforesaid power chamber and the aforesaid delivery chamber;
   d. a connecting means for attaching the aforesaid dispensing nozzle to the object of treatment; and,
   e. a housing in restraining relationship to the aforesaid power chamber and, aforesaid delivery chamber, containing the aforesaid power chamber and delivery chamber.

2. The device according to claim 1 where:
   a. the driving fluid is water;
   b. said osmotic salt is in solid form; and,
   c. the rate-controlling means is a semipermeable membrane.

3. The device of claim 1, where said pouch for containment of the infusate comprises:
   a. a first compartment for storage of infusate in lyophilized form;
   b. a second compartment for storage of pharmaceutically acceptable liquid solvent for said infusate; and,
   c. an impermeable rupturable barrier between said first pouch compartment and said second pouch compartment.

4. The device of claim 1, wherein said infusate pouch is stored with infusate separately from the rest of the device assembly.

5. The device of claim 2, where said activation means is disposed adjacent to, and in contact with said fluid-transporting means.

6. The device of claim 5, where:
   a. said activation means is a plunger or other means of breaking said sealing layer; and
   b. said sealing layer is a foil seal separating the driving fluid from the fluid-transport means.

7. A method for infusing a patient, comprising connecting said patient to a portable osmotic infusion device, said device comprising:
   a. a power chamber comprising:
      a pressure-generating means comprised of a driving fluid;
      a sealing layer separating said driving fluid from a fluid-transport means;
   b. a delivery chamber comprising:
      a pouch containing infusate and a dispensing nozzle;
      an osmotic salt or fluid;
      a rate-controlling means for regulating the volume change of aforesaid pouch;
   c. a fluid-transport means in liquid transmitting relationship between the aforesaid power chamber and the aforesaid delivery chamber;
   d. a connecting means for attaching the aforesaid dispensing nozzle to the object of treatment;
   e. a housing in restraining relationship to the aforesaid power chamber and aforesaid delivery chamber, containing the aforesaid power chamber and delivery chamber;
   f. a means integral with sealing layer or said power chamber for rupturing said sealing layer so that upon rupture of said sealing layer, said driving liquid being transferred by a fluid-transport means from said power compartment to said delivery compartment; and,
   g. activating said device by rupturing said sealing layer.

8. A method according to claim 7 where said pouch containing infusate and dispensing nozzle is incorporated into said device shortly before activation.

9. The device of claim 7, where said pouch for containment of the infusate comprises:
   a. a first compartment for storage of infusate in lyophilized form;
   b. a second compartment for storage of pharmaceutically acceptable liquid solvent for said infusate; and,
   c. an impermeable rupturable barrier between said first pouch compartment and said second pouch compartment.

10. The device according to claim 1 where the drug contained in the infusate pouch is heparin.

11. The device according to claim 1 where the drug contained in the infusate pouch is insulin.

12. The device according to claim 7 where the drug contained in the infusate pouch is heparin.

13. The device according to claim 7 where the drug contained in the infusate pouch is insulin.

14. The device according to claim 1 where the drug contained in the infusate pouch is fluorouracil.

15. The device according to claim 7 where the drug contained in the infusate pouch is fluorouracil.

16. The device according to claim 1 where the drug contained in the infusate pouch is cisplatin.

17. The device according to claim 7 where the drug contained in the infusate pouch is cisplatin.

18. The device according to claim 1 where the drug contained in the infusate pouch is gancyclovir.

19. The device according to claim 7 where the drug contained in the infusate pouch is gancyclovir.

20. The device according to claim 1 where the drug contained in the infusate pouch is adriamycin.

21. The device according to claim 7 where the drug contained in the infusate pouch is adriamycin.

* * * * *